United States Patent [19]

Reiss et al.

[11] 4,123,654
[45] Oct. 31, 1978

[54] METHOD FOR DETERMINING THE DENSITY OF BODIES BY MEANS OF PENETRATING RAYS AND APPARATUS FOR CARRYING OUT SAID METHOD

[75] Inventors: Karl-Hans Reiss; Klaus Killig, both of Erlangen, Germany

[73] Assignee: Siemens Aktiengesellschaft, Berlin & Munich, Germany

[21] Appl. No.: 729,461

[22] Filed: Oct. 4, 1976

[30] Foreign Application Priority Data

Oct. 3, 1975 [DE] Fed. Rep. of Germany ....... 2544354

[51] Int. Cl.² .............................................. G01N 23/20
[52] U.S. Cl. .................................... 250/272; 250/273
[58] Field of Search ........... 250/272, 273, 274, 277 R, 250/278, 279

[56] References Cited

U.S. PATENT DOCUMENTS

| | | | |
|---|---|---|---|
| 2,670,401 | 2/1954 | Weinberg | 250/363 R |
| 2,997,586 | 8/1961 | Scherbatskoy | 250/273 |
| 3,769,507 | 10/1973 | Kenney | 250/272 |
| 3,927,318 | 12/1975 | Macovski | 250/272 |
| 3,961,186 | 6/1976 | Leunbach | 250/272 |

*Primary Examiner*—Craig E. Church

*Attorney, Agent, or Firm*—Hill, Gross, Simpson, Van Santen, Steadman, Chiara & Simpson

[57] ABSTRACT

In the illustrated embodiments radiant energy at a plurality of distinct energy levels (each above 150 keV) is directed along one or more primary beam paths, and a series of detectors are arranged to receive scatter radiation from the same or successive points irradiated by the primary beam energy, with the detectors either collecting scatter energy over identical solid angles and at identical mean scattering angles or having their respective outputs equalized to a common scattering sample for each respective scatter energy spectrum. By relatively shifting a group of detectors a linear or layer region can be scanned, and the respective outputs from each detector can be individually recorded for subsequent processing to eliminate the effects of multiple scattering and unequal mean scattering angles. With detectors stationary, a time series of respective output signals from each detector can be recorded to facilitate the study of local ventilation of defined zones in the lungs, for example. By suitable processing, the output signals can be converted to numerical density readings and/or an accurate graphical display of density variations in a region of medical interest.

60 Claims, 9 Drawing Figures

METHOD FOR DETERMINING THE DENSITY OF BODIES BY MEANS OF PENETRATING RAYS AND APPARATUS FOR CARRYING OUT SAID METHOD

BACKGROUND OF THE INVENTION

This invention relates to a method and apparatus for determining the density of bodies by means of penetrating rays wherein at least one radiation source means emits rays of different wavelengths, and at least one radiation measuring means forms electric signal values corresponding to the intensities which again issue from the body. Apparatus of this type is known, for instance, from the publication "Medical Application of the Compton Effect" by K. H. Reiss and B. Steinle in "Siemens-Forschungs — und Entwicklungsberichte", Vol. 2 (1973), No. 1, pages 16 through 25.

The simple and impressive thought of using the Compton effect for determining the (electron) density in the interior of bodies, and therefore also in living organisms, has been realized in a medically significant fashion only in exceptional instances up to the present time. This is, for example, the determination of the absolute density of the lungs. Only in this instance has it been possible up to the present time, by employing a simple model, to take into consideration with sufficient precision the losses from the radiation source to the scattering location and from the scattering location to the detector; i.e., the absorption of the radiation (compare the above-cited reference). In the case of randomly shaped bodies, such as bones, for example, the conditions are already so complicated that the correction computations become problematical in themselves. Even in the case of the lungs, the back-scattering method has, until now, been limited to a depth of approximately eleven centimeters (11 cm) in the object. Numerous attempts to use measurements of the Compton-scattering of X-ray energy or gamma rays for determining the absolute density in the interior of bodies have not led to any wider application. The reason for this would essentially be a lack of radiation sources with suitable energy, that is, isotopes with suitable radiation, life and activity.

Nevertheless, there is still a great need for methods enabling one to externally determine the density of interior regions of bodies, such as in the spinal column, for example, without being disturbed by obstacles such as the intestinal vesicles. The liver would also be a medically interesting object for density determination because it is accessible only with difficulty to normal X-ray investigation. For the lungs, a method is desirable for determining the local ventilation of defined zones. It is also desirable, if possible, to be able to obtain the result in the form of a section, even if a rough section, of all parts of interest, such as is disclosed in the U.S. Letters Pat. No. 2,670,401, which, however, has not yet been realized on account of a lack of suitable radiating systems. For radiation therapy with ionizing rays there has also long been the need of being able to determine in a simple manner the density distribution in the interior of a body.

SUMMARY OF THE INVENTION

The object which is the basis of the invention is to disclose a simple realization, which can be carried out with simple means, in a method for determining the density of interior regions of bodies by means of penetrating rays and a device for carrying out said method as specified in the first paragraph of the preceding section. This problem is solved by arranging detector means outside of the beam of rays originating directly from the radiation source means and directing the detectors of the detector means to the location in the body which is to be measured.

In applying the invention, narrow beams of high energy rays, that is, such rays having different energies E, are introduced in the body which is to be examined. As is known, scattering processes occur in the particles of matter struck by said rays along the beam path. These scatterings are then detected over a solid angle $\Delta\Omega$ and at a mean scattering angle $\theta$ to the beam path by means of a collimator (K, FIG. 1). The scattered quanta of an energy E' which have been selected by means of the collimator (K) are counted by means of a detector (D) which is connected to the output side of the collimator. The count rates ($N_s$) which are expected here can be calculated according to known formulas. The result of this is the decisive interrelationship that the count rate ($N_s$) is exactly proportional to the electron density in the selected scatter volume (V). A difficulty here is that the quanta arriving from the scatter volume (V) no longer coincide in their number ($N_s$) with those ($N_o$) emitted from the radiation source (S). An undetermined number of these quanta have been absorbed on the path which has already been penetrated. Likewise, the scattered quanta then suffer an additional loss on the path from the scatter volume (V) to the detector (D). The invention proceeds from the fact that, when using radiations of different energies, and when the remaining conditions remain unchanged, measured quantities can be obtained with which the values remaining constant can be eliminated. A simple method can be, for example, the electronic formation of quotients from the different count rates ($N_s$) for the different energies $E_1$, $E_2$, $E_3$ of the primary rays. It has been shown that, by suitably selecting a plurality of radiations, the corrections for random bodies with a water-like absorption can be determined such that an application of the Compton-scattering for absolute-density determination becomes possible and significant. As already indicated above, one application of particular significance in medical diagnosis is determining the density of bones or other internal organs.

However, given a justifiable expense, sectional images can also be produced — of the lungs, for example, so that evidence concerning the local ventilation can be obtained. The resolutions expected range in an order of magnitude of from 1 centimeter to 2 centimeters (1 to 2 cm).

A realization with X-ray energy is also possible. A strictly monochromatic radiation is indeed mathematically quite easily understandable. Nevertheless, with the polychromatic deceleration (bremsstrahlung) radiation which is conventional in X-ray technology, it can be shown numerically and by computation that deceleration radiation is also applicable for this method, given sufficient prefiltering. The use of deceleration requires less shielding than radioactive sources such as iridium 192 ($Ir^{192}$) and cesium 137 ($Cs^{137}$), for example.

The radiator of an X-ray therapy device may be used as the radiation source. It can contain an X-ray tube, for example, which is operated with two or three voltage levels of about 300,000 volts (300 kV) which are timed to coincide with filtering of the output of the tube by means of a lead (Pb) filter having a thickness of one millimeter (1 mm), and intervening operation at 200,000 volts (200 kV) with the output of the tube being filtered by means of copper (Cu) filter segments of a rotating filter (F, FIG. 1). Additional hardenings of the radiation spectrum do indeed result in the body as a consequence of the filtering; however, the effect is relatively small and can be easily surveyed so that the effect does not bring about any uncertainty in the calculated result.

The evaluation may proceed as in the case of the use of monochromatic radiation. Depending upon the patient thickness, additional corrections can be made in the course of evaluation. These corrections consist in that the multiple scattering is empirically taken into consideration. The measurement of the penetrating rays (transmitted radiation) can also additionally provide information regarding area density $b$—that is, the total absorption of the irradiation and of the radiated scattered rays. This information may be used in order to determine the effective patient thickness.

Moreover, X-ray radiation permits a quite convenient localization by means of a television device such as that frequently employed in X-ray diagnosis at the present time. Instead of an individual detector, a group of detectors can be used. These can then be arranged on the edges of a hexagon with the television pick-up device in the center. The pick-up device may be an X-ray image intensifier, or it may be a primary radiation detector in the case of devices employed exclusively for the purpose of determining density.

All detectors, for example, six such detectors, may be aligned toward a single point along the primary beam path. By shifting the group of detectors, a movement of the point being scanned along the beam path of primary rays is possible. This is expedient, for example, in the case of point-by-point measurements—for example, of the liver, because the count rates are thereby increased.

When a plurality of detectors are used, the intersecting points at the primary beam path may also be aligned successively along the primary beam path. The density distributions occurring along the beam of primary rays can then be simultaneously determined. This can be of interest in order to obtain studies regarding the ventilation of the lungs. If a patient is moved in a crosswise or lengthwise fashion in relation to the arrangement consisting of the radiation source and detectors, side-by-side (FIG. 5), measurements of the density are attained which can be combined into sectional images. The pulses of the discriminator output are recorded, for example, and subsequently processed into a picture in an analog or digital fashion, while the above-indicated correction formulas are evaluated. As already indicated above, the algorithm is simpler than in the case of the known computer tomograph. However, the resolution of the picture in the primary radiation direction is limited by the collimator-resolution. The radiation load is dependent upon the dimensioning, and is probably around two radcentimeter squared (2 Rcm$^2$)(incident dose).

In the construction of devices, particularly for examinations of the lungs, it is expedient to take into consideration the fact that precisely the lungs are very strongly influenced by gravitation. Therefore, the examination should be capable of being carried out in a sitting or a standing position, for example, in a riding seat (12, FIG. 2), which may be straddled by the patient in a riding or astride position. The spinal column, the liver, and other organs can also be favorably examined in this position. However, the application of the invention is also possible with conventional tilting devices (that is, those with a supporting wall which is adjustable between vertical and horizontal positions).

The scanning periods for layer pictures of the liver and bones are actually not limited, since a patient remains still for a sufficient period of time. However, for lung examinations, the devices can be dimensioned such that it is possible to manage with five to seven seconds—that is, with a time requirement within one breathing phase. This can be more readily achieved with a shiftable, preferably motor-driven table for producing one axis of scanning than with a complete encircling of the patient with the tube and detector. This probably is mainly due to the fact that the shields required for the rays and the detector must be very heavy. With a scanning path of approximately thirty centimeters (30 cm), it is favorable, in order to adhere to the above-cited time requirement, to provide a speed of from about five centimeters per second to about ten centimeters per second (5 to 10 cm/sec). The aforementioned riding seat or the standing area on which the patient stands can also be correspondingly constructed for shifting movement (that is, to provide a further motor-driven displacement to provide a further scanning axis).

The multiple scattering which can likewise occur when the invention is used, can be easily calculated. This is indicated in the reference cited above, for example, in Section 2.3 thereof. It is apparent that a fraction of from ten to fifty percent (10 to 50%) multiple scattering can be expected. This leads to a certain falsification of the absolute values. In the pictorial illustration, the fraction of multiple scattering which, as in the case of X-ray diagnosis, makes itself evident on first approach as a uniform veil, can be taken into account by computation by subtracting a specific sum from the measured values, respectively, in the computer.

Other objects, features and advantages of the invention will become apparent from the following detailed description taken in conjunction with exemplary embodiments which are illustrated in the drawings.

DETAILED DESCRIPTION

Introductory Discussion Based on FIGS. 1 and 1A, 1B and 1C

Figure 1:
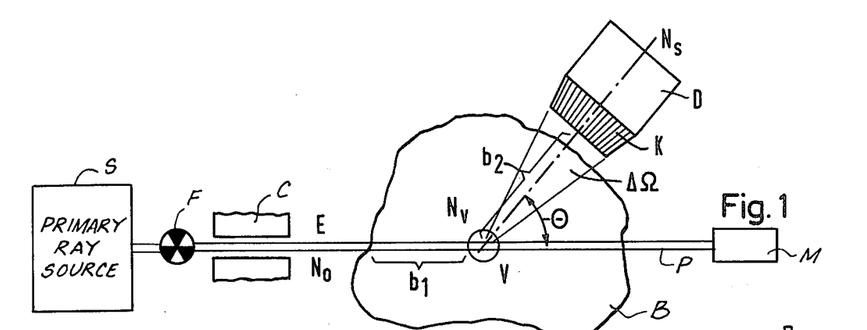
FIG. 1 shows a general fundamental illustration serving for the purpose of introductory discussion in the preceding section hereof.

In the general illustration of FIG. 1, a primary source of penetrating rays of a plurality of wavelengths is indicated at S. The reference letter F designates any desired filter means for eliminating or attenuating undesired constituents of the energy supplied by source S. Reference letter C represents any desired beam-shaping means such as a collimator and/or suitable manually or mechanically actuatable shutter means (such as indicated in figure ten of the aforementioned publication reference). In applying the invention, narrow beams of high energy rays, that is, such rays having different energies E and supplying a number $N_O$ quanta per second, are introduced into the body B, FIG. 1, along a primary path having a area density of $b_1$ grams per centimeter squared, so that a number $N_V$ quanta per second impinge on a scatter volume V, FIG. 1. As is known, scattering processes occur in the particles of matter struck by the rays where the primary path P of the rays intersects the scatter volume V. The scattered rays are then detected over a solid angle $\Delta\Omega$ which is disposed at a mean scattering angle $\theta$ by means of a collimator K, FIG. 1. The scattered rays are indicated in FIG. 1 as traversing a path having a area density of $b_2$ grams per centimeter squared. The scattered quanta of energy $E'$ which are transmitted by the collimator K are then counted by means associated with detector D, FIG. 1. The detected counting rate is generically represented by the symbol $N_s$, FIG. 1. Details of a sodium iodide crystal scintillation detector are given in connection with the tenth figure of the aforementioned publication reference, such crystal being coupled with a photomultiplier and counter. The count rates $N_s$ which are expected here in response to an incident value $N_V$ can be calculated according to known formulas. The result of this is the decisive interrelationship such that the electron density in the scatter volume V can be determined in theory from the measured count rate $N_s$. In the present specification, the electron density in electrons per gram is represented by the symbol $\nu$. The density in grams per centimeter cubed is expressed by the symbol $\rho$. Thus, in theory, the measured count rate $N_s$ is exactly proportional to the electron volume density corresponding to the product $\rho \cdot \nu$. A difficulty in practical application is that the quanta $N_V$ arriving at the scatter volume V, FIG. 1, no longer coincide in their number with those ($N_O$) emitted from the radiation source S. An undetermined number of these quanta have been absorbed on the primary path which has already been penetrated in advance of scatter volume V. Likewise, the scattered quanta then suffer an additional loss on the path from scatter volume V to detector D. The invention proceeds from the fact that, when using radiations of different energies, and when remaining conditions are constant, measured quantities can be obtained with which the values remaining constant (such as, surface densities $b_1$ and $b_2$) can be eliminated. A simple method can be, for example, the electronic formation of quotients from the different count rates $N_s$ for the different energies such as $E_1$, $E_2$, $E_3$ supplied from the source S. It has been shown that, by suitably selecting a plurality of radiations, the corrections for random bodies with a water-like absorption can be determined such that an application of the Compton-scattering for absolute-density determination becomes possible and significant. As already indicated, one application is of particular significance in medical diagnosis where quantitative density values for bones or other internal organs can be utilized as variously described in the reference publication mentioned above. However, given a justifiable expense, sectional images can also be produced—of the lungs, for example, so that evidence concerning the local ventilation can be obtained. The resolutions expected range in an order of magnitude of one to two centimeters (1 to 2 cm)(for example, between successive scattering volumes such as indicated at $V_1$, $V_2$, $V_3$ ... $V_n$ in FIG. 1A).

While, in the foregoing description, a source S may be considered as supplying discrete selected quantum energies $E_1$, $E_2$, $E_3$, a realization of FIG. 1 with X-rays is also possible. A strictly monochromatic (that is, monoenergetic) radiation is indeed mathematically quite easily understandable. Nevertheless, with the polyenergetic deceleration bremsstrahlung which is conventional in X-ray technology, it can be shown numerically and by computation that deceleration radiation is also applicable for this method, given sufficient prefiltering as represented at F in FIG. 1. Deceleration radiation requires less shielding than radioactive iridium and cesium, for example.

The evaluation may proceed as in the case of the use of monochromatic radiation. Depending upon the patient thickness, additional corrections can be made in the course of evaluation. These corrections consist in that the multiple scattering is empirically taken into consideration. The measurement of the penetrating rays can also additionally provide information regarding surface density $b$ grams per centimeter squared—that is, the total absorption of the irradiation due to surface density $b_1$ along the primary path and surface density $b_2$ for the path of the scatter rays. This information may be used in order to determine the effective patient thickness.

Figure 1A:
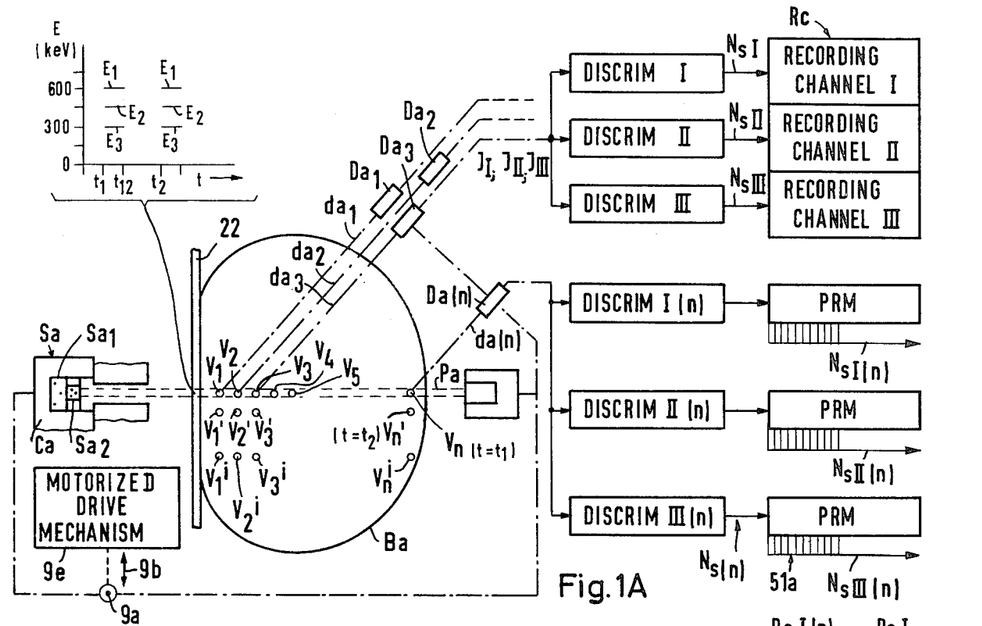
FIG. 1A is a diagrammatic view similar to FIG. 1, but illustrating an embodiment wherein the primary ray source means comprises respective radioactive isotopes in a common radiation shielding container.
Figure 1B:
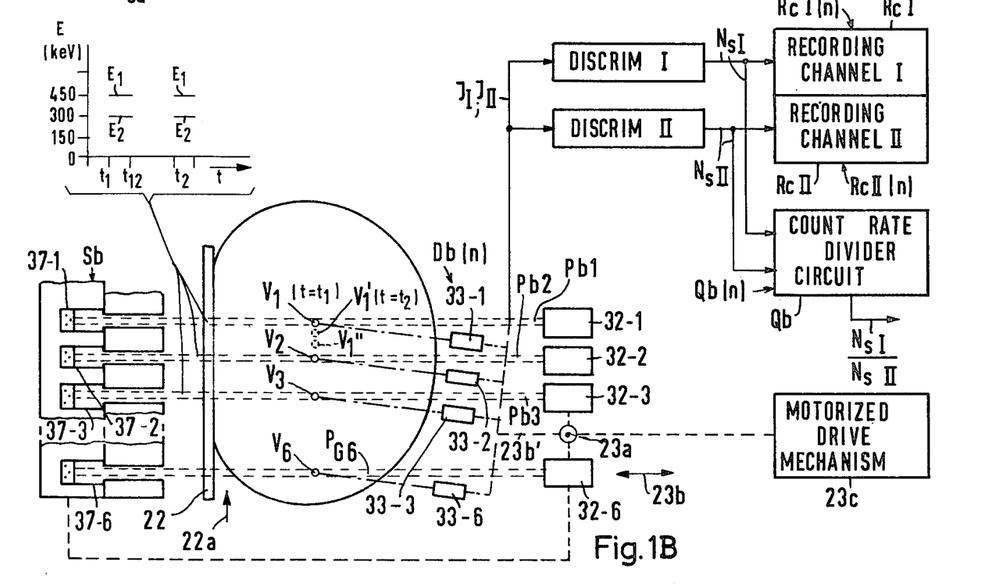
FIG. 1B is a view similar to FIG. 1A, but illustrating the simplified case where a single radioactive isotope provides two radiation energy levels with respective corresponding wavelengths.
Figure 1C:
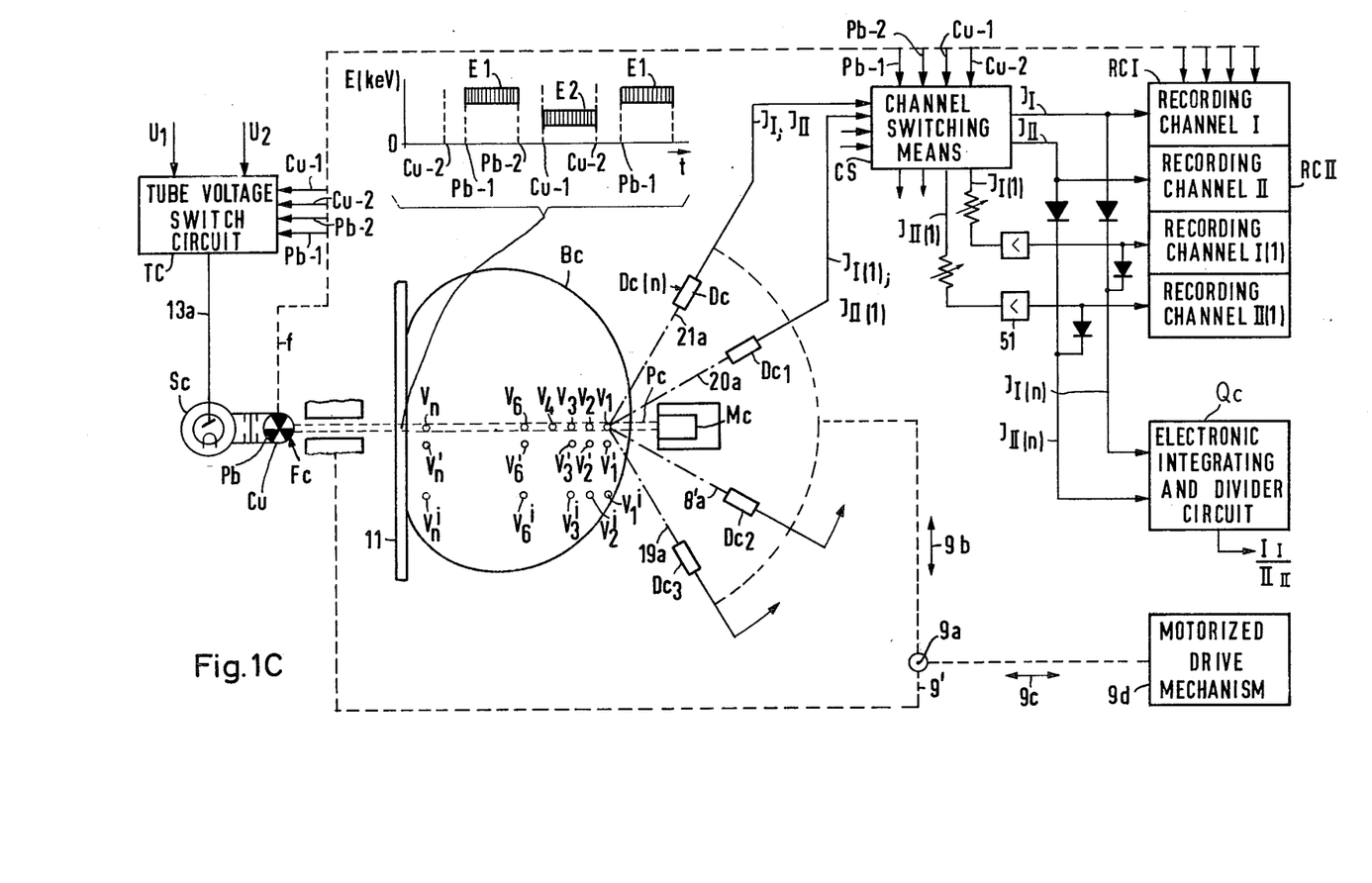
FIG. 1C illustrates an embodiment wherein the radiation source means is a periodically varied source of polyenergetic deceleration radiation.

FIGS. 1A through 1C illustrate exemplary embodiments pursuant to FIG. 1. FIGS. 1A through 1C also indicate conventional components by means of labeled rectangles. The nature of such components as being in themselves conventional is apparent from a consideration of the aforementioned publication reference.

Referring to FIG. 1A, for a measurement with three different radiations $E_1$, $E_2$, $E_3$, two pills sa1 and sa2 are positioned one behind the other within a chamber of a radiation-shielded container ca, FIG. 1A. Pill sa1 of the shielded chamber may be four millimeters by four millimeters in cross section (4 × 4 mm²) and contain an activity of 37 × 10¹⁰ per second (ten Ci) cesium 137 (Cs¹³⁷). The other pill sa2 in the chamber may consist of iridium 192 (Ir¹⁹²) with an activity of 111 × 10¹⁰ per second (thirty Ci) and with a cross section of two millimeters by two millimeters (2 × 2 mm²). By way of a specific example, FIG. 1A may be taken as representing a series of detectors $D_{a1}, D_{a2}, \ldots D_{a(n)}$ for simultaneously sensing density at respective scatter volumes $V_1, V_2, V_3 \ldots V_n$ of an internal region of a body B. Each detector may be of the type indicated in the tenth figure of the cited publication reference so as to respond to scattered energies $E_I, E_{II}, E_{III}$ to supply respective proportional amplitude pulse signals $J_I, J_{II}, J_{III}$ which can be discriminated by the conventional techniques such as pulse height discrimination as represented by components DISCRIM. I, DISCRIM. II, DISCRIM. III, FIG. 1A. By solving simultaneous equations using the respective measured count rates $N_{SI}, N_{SII}, N_{SIII}$, and applying the known scattering cross sections and mass attenuation coefficients, it is possible to obtain the area densities $b_1$ and $b_2$ on the path from source $S_a$ to the scattering location $V_n$ and from the scattering location to the detector $D_{a(n)}$, and it is then also possible to calculate the density $\rho_{V(n)}$. Since the isotopes given in the example of FIG. 1A are quite expensive, it is also possible to employ a simplified method as represented in FIG. 1B, for example.

In the example of FIG. 1B, one proceeds from the fact that the values of absorption as referred to mass density for the primary path to the scatter volume and for the scatter path, namely, the mass attenuation coefficients $(\mu/\rho)$ and $(\mu/\rho)'$ for the forward scattering, with angle $\theta$ not greater than forty-five degrees (about 30° to 45°) due to the Compton formula, and for water, differ only slightly. Therefore, the desired correction can also be achieved with two radiations $E_1$ and $E_2$ as shown in FIG. 1B. For this purpose, iridium 192 ($Ir^{192}$), for example, can be used, as indicated at sb in FIG. 1B, such single isotope providing radiations of quantum energies of 310,000 electron volts (310 keV) and 468,000 electron volts (468 keV). However, one must restrict oneself here to calculating the sum of the area densities $b_1$ and $b_2$. Even this magnitude does not suffice in order to arrive at the density in the scatter volume such as $V_1$. The measurement of the count rates can proceed behind the same collimator $K_b$ with the same detector $D_{b(n)}$ as for FIG. 1A. Here, discriminators DISCRIM. I and DISCRIM. II are provided which only allow signals corresponding to the respective energy levels $E_I, E_{II}$ to reach respective recording channels RCI and RCII. Further, the outputs of the discriminator circuits are supplied to respective inputs of a count rate divider circuit $Q_b$. By dividing the count rates $N_{SI}$ to $N_{SII}$ to obtain a quotient such as $N_{SI/N_{SII}}$ it is possible to obtain the area density $b$ in the case of known irradiation rates $N_{O_1}, N_{O_2}$ as well as the likewise known scatter cross-sections, and the mass attenuation coefficients $(\mu/\rho)_I$ and $(\mu/\rho)_{II}$. Accordingly, count rate divider circuit $Q_b$ may supply a area density value $b$ as indicated in FIG. 1B, and from this value $b$, it is then possible to obtain the density $\rho$ in the scatter volume from the following formula:

$$\rho = \frac{C}{V} \times \frac{N_{SI}}{N_{OI}} \times \exp\left[(\frac{\mu}{\rho})_I \times b\right]$$

In this formula, C is an apparatus constant which results from the magnitudes pertaining to the apparatus, such as the conversion constants of the detector and the transmission constants of the collimator. As previously, the symbol $\nu$ refers to electron density in electrons per gram. For the case where mass density $\rho$ is equal to about one gram per centimeter cubed, the volume electron density is about $3 \times 10^{23}$ electrons per centimeter cubed. The symbol $N_{SI}$ is the number of the scatter quanta with respect to the scatter angle $\theta$ and within the solid angle $\Delta\Omega$, given the scatter energy value $E_I$. The above formula is, of course, also applicable for the incident energy $E_2$ which gives rise to a scattered energy (average) $E_{II}$, a count rate magnitude of $N_{SII}$ resulting, and so on. By way of example, the variables N, such as $N_{OI}$ and $N_{OII}$ may be taken as the respective numbers of primary quanta per square centimeter of primary beam cross-section and per second. The magnitude $(\mu/\rho)_I$ and the magnitude $(\mu/\rho)_{II}$ represent the mass attenuation coefficients for the primary radiation of energy levels $E_1$ and $E_2$, respectively.

FIG. 1C is an illustration of an example utilizing an X-ray source $S_c$. For exmple, the radiator $S_c$ may be an X-ray therapy device comprising an X-ray tube, for example, which sequentially receives voltages $U_1$ and $U_2$ in step with the rotation of the rotating sector filter $F_c$. For example, the potential $U_1$ may be approximately 300,000 volts (300 kV) and potential $U_2$ may be approximately 200,000 volts (200 kV). The potential $U_1$ may be synchronized with control of the beam by means of the sectors Pb which may be of lead one millimeter thick (1 mm). The potential $U_2$ may be synchronized with the segments Cu of filter $F_c$, and these segments may be of copper three millimeters thick (3 mm). Additional hardenings do indeed result in the body $B_c$ as a consequence of the filtering; however, the effect is relatively small and can be easily surveyed, so that the effect does not bring about any uncertainty in the calculated result. As indicated by the dash line $f$ in FIG. 1C, the operation of the rotating filter $F_c$ may be synchronized with that of the tube voltage switching circuit component $T_c$ and with the channel switching means CS so that the respective signals from each detector corresponding to the respective levels of operation of the source $S_c$ are supplied to respective recording channels such as RCI and RCII, and so that the respective outputs are supplied to respective inputs of an electronic divider circuit $Q_c$. As taught by Reiss U.S. Pat. No. 3,924,133, the voltage levels $U_1$ and $U_2$ may be produced with a first source of $(U_1 + U_2/2)$ (for the present invention, 250kV), and a second source of $(U_1 - U_2/2)$ (here 50kV) which is cyclically added (to give 300kV) and subtracted (to give 200kV). Each detector $Dc(n)$ in FIG. 1C may comprise a photomultiplier such as shown by reference numeral ten in the Reiss U.S. Pat. 3,924,133, which serves to transmit the successive momentary intensities $J_I$ and $J_{II}$ and is connected with means such as shown in the second figure of said Reiss U.S. patent for switching to respective integrator circuits (36) and (37) which integrate such signals with a suitable time constant to provide successive corresponding integrated signals $I_I$ and $I_{II}$, these signals being divided by means of a bridge circuit to supply quotient signals such as $I_I/I_{II}$, FIG. 1C. The measurement of the transmitted radiation along the path $P_c$ is indicated by component $M_c$ in FIG. 1C. The multiple scattering is empirically taken into consideration, while the measurement of the penetrating rays at $M_c$ can also additionally provide information regarding area density $b$—that is, the total absorption of the irradiation and of the scattered rays. This information may be used in order to determine the effective patient thickness. Moreover, X-ray radiation permits a quite convenient localization by means of a television device (such as indicated by reference numeral nine in said Reiss patent) with sequential or selective display of radiation levels as taught in U.S. Pat. No. 3,904,874, for example.

The group Dc(n) of detectors such as Dc, $D_{c1}$, $D_{c2}$, $C_{c3}$ of FIG. 1C can be arranged on the edges of a hexagon with the television pick-up such as represented at $M_c$ in the center. The pick-up device $M_c$ may be an X-ray image intensifier or it may be a primary radiation detector in the case of devices employed exclusively for the purpose of determining density on a quantitative or numerical basis. All detectors, such as six detectors, may be aligned on a common scatter volume as $V_1$ of the irradiated beam of rays, or respective detectors may be aligned with respective scatter volumes such as $V_1$, $V_2$, $V_3 \ldots V_6$, FIG. 1C. In this latter case, by moving the detectors as a group along with source Sc and pick-up device Mc, successive contiguous regions including that indicated at $V_1'$-$V_6'$ and so on, may be scanned up to a region $V_1^i$—$V_6^i$, FIG. 1C. Where all six detectors are aligned simultaneously with a given scatter volume such as $V_1$, the detectors may be moved as a group along the beam path $P_c$, and such point-by-point measurement may be suitable, for example, in the measurement of density of the liver. With FIGS. 1A and 1B, point-by-point measurement enables an increase in the measured count rates, while in FIG. 1C the total signal intensities, such as $J_{I(n)}$, $J_{II(n)}$, are increased.

Detailed Description of FIGS. 2-6

Figures 2, 3, 5:
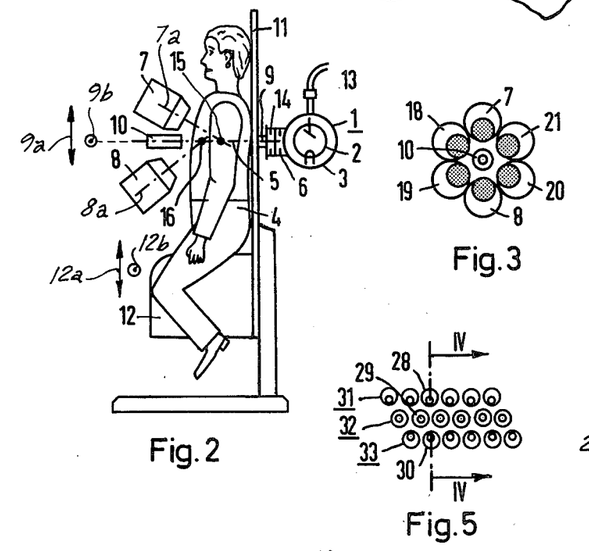
FIG. 2 illustrates a density measuring apparatus utilizing the principles of FIG. 1C and wherein forward scattering is sensed at two successive points along the primary beam path by the use of two detectors.
FIG. 3 illustrates a diagrammatic cross-sectional view based on the embodiment of FIG. 2, but with the addition of four further detectors, and with the detectors being aligned with successive points along the primary beam path, and each operating as illustrated in FIG. 1C, for example; and having processing and recording circuitry as indicated in FIG. 1C.
FIG. 5 illustrates a diagrammatic sectional view of the detector arrangement of FIG. 4, taken generally along the line V—V of FIG. 4.

The arrangement according to FIG. 1 is illustrated in FIG. 2 in a technical embodiment. As the radiation source 1, an X-ray tube 2 is used which is mounted in a casing 3 which is impervious to rays. The beam of X-ray energy 5 supplied to patient 4 is shaped by means of a diaphragm arrangement 6. Radiation source 1 as well as the arrangement of detectors 7 and 8 are mounted on a supporting arm 9. A detector 10 for transmitted rays is also mounted on the arm 9. Supporting arm 9 extends about one side of a patient support wall 11 and ridigly connects components 1, and 7, 8, 10 for joint vertical movement as represented by the double headed arrows 9a, and also supports the components for horizontal movement as represented by 9h in FIG. 2, such that path 5 can be moved from one side to the other of the patient, and can be moved in successively offset vertical planes over the extent of organs of interest, such as the lungs. The patient 4 is preferably seated astride a saddle 12 in a riding position or straddle position. The patient support means 11, 12 is preferably also adjustable in a vertical direction as represented by double headed arrow 12a and in a crosswise or horizontal direction as indicated by a reference numeral 12b. Tube 2 receives its supply current via a supply line 13. Supply line 13 includes a conductor 13a, FIG. 1C, which comes from a tube voltage switching circuit $T_c$, FIG. 1C. Respective supply voltages $U_1$ and $U_2$ are alternatey connected with conductor 13a by means of the circuit $T_c$ and the X-ray tube 2 is otherwise operated in a known fashion.

During operation of the system of FIG. 2, the X-ray beam 5 is kept at the desired diameter by means of diaphragm elements indicated diagrammatically at 6. Moreover, an additional filter 14 is provided which may conform with that of FIG. 1C, for example. In such embodiment, the potential $U_1$ is 100,000 volts (100 kV) higher than the voltage $U_2$, and the filter 14 introduces a much greater attenuation into the path of the X-ray energy during application of the potential $U_1$, so that the energy spectrum associated with the intervals of the potential $U_1$ are relatively distinct from the energy spectrum associated with the potential $U_2$, and so that the scatter rays which are scattered at scatter volumes such as 15 and 16, FIG. 2, have a much higher average energy during the high energy operation of source 1 than during the relatively lower energy intervals of operation of source 1. The detectors 7 and 8 are shown as having detector axes 7a and 8a which form respective mean scattering angles corresponding to angle $\theta$ in FIG. 1 relative to the axis or path of beam 5. The collimator corresponding to collimator K of FIG. 1 of detector 7, FIG. 2, is arranged to transmit scattered energy from scatter volume 15 to the associated detector, and similarly the collimator for detector 8 is arranged to transmit essentially only scattered energy from the scatter volume 16. Detector 10 picks up those rays which pass directly through the body of patient 4. Detector 10 can be a scintillation counter, counter tube, or also an image intensifier, which can simultaneously serve the purpose of localizing the measured direction.

The illustrated arrangement of FIG. 2 is advantageous vis-a-vis present methods because all linear fluctuations of the electrical values of the X-ray tube 2 as well as of the radiation measurement means 7, 8, 10 compensate one another to a great extent. Thus, if the power supply voltage (mains voltage) fluctuates so as to cause a fluctuation of the potentials $U_1$ and $U_2$, and if the sensitivity of the radiation measurement means 7, 8, 10, or the emission current of the X-ray tube 2, respectively, is thereby changed, these changes would be insignificant because they take effect equally for both the high energy and the low energy spectra received sequentially by each of the detectors 7 and 8. Referring to FIG. 1C, if the detector $D_c$ is taken as corresponding to the detector 7, and also to the detector 8, it will be seen that the channel switching means CS supplies the current pulse $J_I$ to one output line during each high energy level of operation of tube 2, and supplies the alternate electrical pulse $J_{II}$ to the other output line. The electrical pulses $J_I$ and $J_{II}$ corresponding to the pulses of high and low scattered energy as collected by each of the detectors may be supplied to an electronic integrating and divider circuit component as indicated at $Q_c$, the pulse $J_I$ producing an integrated intensity $I_I$ whose amplitude may correspond to the integral of the pulse $J_I$, and the pulse $J_{II}$ producing an integrated intensity $I_{II}$. Where the component $Q_c$ forms the quotient such as $I_I/I_{II}$, the quotient value will not be altered by fluctuations which have a linear effect on the high energy and low energy spectra. However, as a rule, possible fluctuations of the voltages $U_1$ and $U_2$, even though proportionate, could effect the radiation intensities in a stronger than linear fashion. Therefore, it is only necessary to provide means for maintaining the constancy of these applied voltages $U_1$ and $U_2$ within the framework of the desired measuring accuracy.

In an arrangement according to FIG. 3, in addition to detectors 7' and 8', further detectors 18 through 21 are arranged about central detector 10. Where detectors 7' and 8' are aligned with points 15 and 16 along the path of beam 5 within the patient, detectors 18 through 21 can register with scatter radiations from other scatter volumes along the path of beam 5 within the patient. Thus, with six detectors, measurement at six successive depths within body 4 can thereby take place. If the arm 9, for example, is moved at a constant rate in the vertical direction, such six points such as 15 and 16 along the beam path within the patient can also be progressively shifted in a vertical sectional plane, so that successive signals from each of the detectors can be combined to form a density-sectional view in the vertical plane coinciding with the path of beam 5. By adjusting the arm 9 in a horizontal plane as represented at 9b, and again carrying out a vertical scanning movement as represented by arrow 9a, any desired other vertical sectional view may be obtained.

As an alternative, all detectors, for example each of the six detectors of FIG. 3, may be aligned with a common point such as 15 in FIG. 2 or such as indicated at $V_1$ in FIG. 1C. In FIG. 1C, successive detectors $D_c$, $D_{c1}$, $D_{c2}$, and $D_{c3}$ are indicated which may generally correspond with the detectors indicated at 21, 20, 8' and 19 in FIG. 3 in being disposed at successive equal angles about a central path such as $P_c$ when viewed in a vertical plane. FIG. 1C is intended to represent a generally horizontal plane, and the arrow 9b in FIG. 1C thus indicates a horizontal axis of movement corresponding to axis 9b of FIG. 2, while the double headed arrow 9c in FIG. 1C indicates a horizontal axis of scanning movement parallel to the path $P_c$ which corresponds to the axis of beam 5 in FIG. 2.

The detectors in FIG. 1C have been indicated as having respective detector axes 21a, 20a, 8'$_a$ and 19a forming respective mean scattering angles $\theta_c$, $\theta_1$, $\theta_2$, and $\theta_3$ which in the embodiment with a common scatter volume $V_1$ may all be equal and may have values of less than 45°, for example equal angles in the range from about 30° to 45°. For the case where detectors such as $D_{c1}$, $D_{c2}$, and $D_{c3}$ are arranged in a common vertical plane but are aligned with respective adjacent scatter volumes such as $V_1$, $V_2$ and $V_3$, the angles $\theta_1$, $\theta_2$ and $\theta_3$ will be different, but may still lie within a range such as from about thirty degrees to forty-five degrees. For the sake of a diagrammatic indication, a motorized drive mechanism is indicated at 9d in FIG. 1C; such mechanism may be coupled with the arm 9 indicated in FIG. 2 so as to provide scanning movement at a constant rate in any one or more of the directions of arrows 9a, 9b, and 9c, for the purpose of carrying out any desired scanning sequence.

With the particular embodiment illustrated in FIG. 1C, where six detectors are directed toward a common point such as VP, the clearances are such between the patient space and the source and detector components that mechanism 9d may move the arm 9 in the direction of arrow 9c so as to scan successive volumes $V_1$, $V_2$, $V_3$, $V_4$ and so on in time sequence, the successive pulses $J_I$ and $J_{II}$ from each detector being recorded on respective channels such as channels I and II designated by RCI and RCII in FIG. 1C. The operation of the recording channels may be synchronized with the operation of the other components as indicated by the dash line so that transitional intervals in the operation of the filter $F_c$ can be identified with respect to the recorded signals during subsequent processing. Similarly, channel switching means such as CS may receive four input signals P$b$-1, P$b$-2, C$u$-1, C$u$-2, the signal Pb-1 indicating that a lead (Pb) sector is fully covering the beam path, and the signal Pb-2 signifying the beginning of any transition between such a Pb sector of filter $F_c$ and the beginning of a complete copper filtering as signified by Cu-1. Similarly signal Cu-2 signifies the end of a complete copper filtering interval and the beginning of a transition to a lead filtering, the next complete lead filtering interval being introduced by the signal Pb-1, and so on. It will be apparent that a commutator device may rotate in synchronism with filter $F_c$ so as to provide signals P$b$-1, P$b$-2, C$u$-1, C$u$-2 at the proper instants in the cycle of the filter $F_c$, the signal Pb-1 serving to connect the detector with recording channel I, the signal Pb-2 serving to open the channel switching means, the signal Cu-1 serving to connect the detector with recording channel II and the signal Cu-2 serving to again open circuit the channel switching means, so that uniform samples of the high level and low level scattered energy spectrums are distributed to the recording channels RCI and RCII and to the circuit component $Q_c$. The same four signals may be supplied to a separate channel of the recording system RC, for example. Signals Pb-1 and Cu-1 are shown as being supplied to switching circuit component $T_c$, the signal Pb-1 connecting potential $U_1$ with tube 2 and the signal Cu-1 connecting potential $U_2$ with the tube.

The same point-by-point scanning with a plurality of detectors as indicated in FIG. 1C can be performed with the source means of FIG. 1A or FIG. 1B, utilizing the respective associated detector processing component as indicated in FIG. 1A or FIG. 1B.

With the use of switching circuitry (13) of the first figure of U.S. Pat. No. 2,924,133 in the embodiment of FIG. 1C, the time required to shift the reversing contacts (23) may correspond to the interval Cu-2 to Pb-1, and to the interval Pb-2 to Cu-1. In this case, reversing of the contacts can begin at times Cu-2 and Pb-2, but the energy spectra E1 and E2 will actually be produced beginning at Pb-1 and at Cu-1 as indicated by the energy-time diagram (keV as a function of time) shown associated with path $P_c$ in FIG. 1C.

Figure 4:
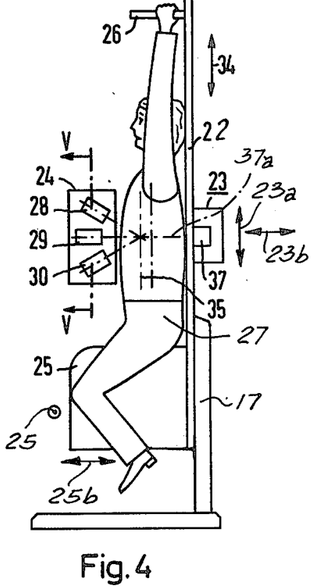
FIG. 4 illustrates an arrangement with eighteen detectors arranged superimposed in three rows, the upper and lower rows operating according to either the embodiment of FIG. 1A or the embodiment of FIG. 1B; and each detector having the corresponding processing and recording circuitry of FIG. 1A or FIG. 1B.

In an arrangement according to FIG. 4, a supporting wall 22 is used, and with a support arm corresponding to support arm 9 maintaining rigid alignment between radiation source 23 and detector arrangement 24, while providing for joint movement thereof in a longitudinal (vertical) direction as indicated by arrow 23a and in a crosswise (horizontal) direction as indicated at 23b in FIG. 4. Moreover, a rider seat 25 together with a supporting handle 26 is likewise movably adjustable relative to a supporting frame 17, so that the patient 27 sitting upon said seat can also engage in movements such as are indicated by arrow 25a and 25b, for example. In the detector arrangement 24, which is illustrated as a section through the arrangement illustrated in FIG. 5 along line IV—IV, there are 18 detectors, of which those in FIG. 4 which are designated with reference numerals 28, 29 and 30 become visible. The remaining detectors are arranged in rows 31, 32, 33, six detectors being arranged next to one another in each row, and the detectors of the successive rows being staggered relative to one another such that the detector which is designated by reference numeral 28 in row 31, and which represents the third in its row, and the one that is designated by reference numeral 30 in row 33 and which is the second in its row, are located one beneath the other. By shifting the patient 27 in the direction of double arrow 34, a layer recording of the density distribution in plane 35 of patient 27 can be obtained. By disposing the detectors of arrangement 24 along horizontal lines such that the six detectors which are next to one another result in a width of 35 centimeters - for example, by using eighteen crystals at about 3 inch centers and by shifting the detector array 24 in the direction of arrow 23a over a vertical distance of 35 centimeters within a time interval of 5 seconds - a vertical plane such as indicated at 35 in FIG. 4 in the lungs can be scanned and can be recorded as indicated at RC in FIG. 1A or FIG. 1B, for example. As the actual radiation source, isotope radiators are arranged in housing 23 as diagrammatically indicated in FIG. 1A. Thus, as described with respect to FIG. 1A, pill 37 indicated in FIG. 4 may contain the isotopes Ir$^{192}$ (iridium 192) and Cs$^{137}$ (cesium 137), for example. An advantage of the embodiment of FIG. 4 is that no high voltage device is required, the rays being produced by means of isotopes. It is expedient to select the composition of the isotopes such that they produce comparable count rates at the outputs of the respective discriminators, FIG. 1A.

FIG. 1A, while indicating the use of two isotopes and three energy levels which differ successively from each other by at least 100,000 electron volts (100 keV), in conformity with the preferred teaching for FIG. 4, illustrates the use of a ring of detectors corresponding to FIG. 3 with the axes thereof $da1, da2, da3, da4, da5, da(n)$ being directed to successive scatter volumes $V_1, V_2, V_3, V_4, V_5, V_n$ along the path $P_a$ of the rays within the body B. In this respect, FIG. 1A is similar to the arrangement of FIG. 2, and a motorized drive mechanism is indicated at 9e for producing a relative shifting movement along axes 9a and 9b which conform with the vertical and horizontal axes of FIG. 2. Thus, for example, if the motorized drive mechanism 9e produces a uniform scanning movement along a horizontal axis 9b, the detectors scan successive regions such as indicated at $V_1$-$V_n$, $V_1'$-$V_n'$, through a region as indicated at $V^i_1$-$V^i_n$.

In FIG. 1B, the arrangement of a source $S_b$ and detectors may conform with that of FIG. 4 and 5 except that FIG. 1B utilizes the example of a single isotope supplying two distinct energy levels $E_1$ and $E_2$ which have an energy difference of at least 100,000 electron volts (100 keV). Thus, the successive shielded chambers 37-1 through 37-6 in FIG. 1B conform with the chamber 37 of FIG. 4 and are in alignment with respective transmittance detectors such as 29 in FIG. 4, the sucessive in line detectors being designated 32-1 through 32-6 in FIG. 1B so as to indicate their correspondence with row 32 of FIG. 5. Similarly, detectors 33-1 through 33-6 in FIG. 1B correspond to the lower row of detectors designated 33 in FIG. 5. As indicated for detector 30 in FIG. 4, the detectors 33-1 through 33-6 in FIG. 1B may form acute angles with the respective ray paths $P_{b1}$-$P_{b6}$, the means scattering angles $\theta_1$ through $\theta_6$ for the detectors 33-1 through 33-6 being equal for an embodiment corresponding to FIGS. 4 and 5, and the corresponding upper row of detectors also having equal mean scattering angles corresponding and equal to the angles $\theta 1$ through $\theta 6$. By way of example, for the case of two energy levels $E_1$ and $E_2$, the angles $\theta_1$ through $\theta_6$ and the corresponding angles for the upper row of the detectors may be below forty-five degrees and preferably in a range from about thirty degrees to forty-five degrees.

In FIG. 1B, a motorized drive mechanism 23c has been indicated for operating the embodiment of FIG. 4 along the axes indicated at 23a (vertical) and 23b, so as to indicate that the embodiment of FIG. 1B may conform with the embodiment of FIG. 4 with respect to patient mounting and directions of possible scanning movement.

In any of the embodiments involving isotopes, suitable remotely controlled shutter mechanisms may be provided for shutting off radiation until the actual beginning of a scanning cycle, and for again shutting off radiation at the end of a desired scanning cycle, such as $t_1$ or $t_2$, FIGS. 1A, 1B.

Figure 6:
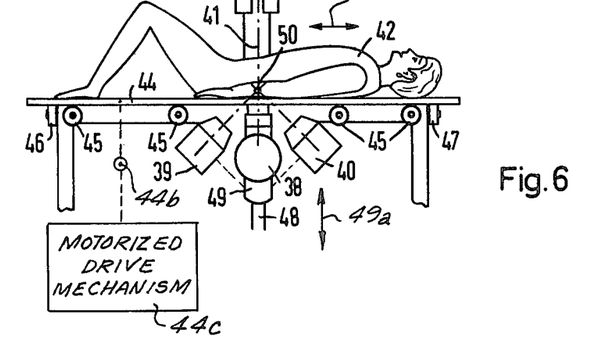
FIG. 6 illustrates an arrangement in which back-scatter radiation is utilized, operation otherwise being in accordance with the embodiment of FIG. 1C.

In an arrangement according to FIG. 6, use is made of back scattering. As is known, radiation scatters to all sides, so that detectors can also be mounted next to the radiation source such as indicated at 38 in FIG. 6. In FIG. 6, detectors 39 and 40 are shown mounted on opposite sides of an X-ray source 38. Both detectors 39 and 40 are aligned with the path of the beam of primary rays 41 issuing from a radiator 38. The intersection point or points are situated in the body of the patient at a desired region. In order to prevent undesired radiation, any of the embodiments may be provided with a transmission detector which includes a radiation collector such as indicated at 43 consisting of a highly radiation-absorbing material, such as lead. As in the preceding embodiments, collector 43 is in alignment with the axis 41 of the primary beam path and may include a transmission monitor such as any of those previously referred to. In order to provide the movement possibilities such as have been described in the case of the embodiments of FIGS. 2 and 4, a patient-supporting table 44 is mounted on rollers 45 which make possible shifting in a longitudinal direction as indicated by arrow 44a, FIG. 6. Lateral rollers are provided such as rollers 46 and 47 for accommodating a shifting in the crosswise direction such as indicated by axis 44b. For the sake of diagrammatic illustration, a motorized drive mechanism is indicated at 44c which is mechanically coupled with table 44 to produce the motion represented by arrow 44a. The arrangement consisting of radiator 38 and detectors 39, 40, is shiftable along a stand column 48 by means of a shift sleeve 49. Thus, intersection point 50 which is shown as being the common intersection point for the detector axes of detectors 39 and 40, is shown located above plate 44 of the table, and can be placed in different regions of the body of a patient 42.

Basically, the measurements can be carried out in the same way in each of the embodiments. The main difference consists solely in the actual relative arrangement of the radiator and detectors. In each of the embodiments, the pulses of the discriminator output, or the respective pulses from a channel switching means or the like, for each of the plurality of detectors, or for detector means assuming a sequence of positions relative to one or more beam paths, are recorded, for example, and subsequently processed into a picture in an analog or digital fashion, while the above-indicated correction formulas are evaluated so as to obtain numerical absolute density readings for the successive scatter volumes which are scanned. The various motorized drive mechanisms 9d, 9e, 23c and 44c may be adapted to provide a uniform scanning speed selectable in the range from about (5 to 10 cm/sec) per second. The riding seat such as 12 or 25, or a corresponding standing area on which the patient stands can also be correspondingly constructed for uniform movement at such scanning speed. As previously indicated, in developing a pictorial illustration of a scanned area, the fraction of multiple scattering, which makes itself evident on first approach as a uniform veil, can be taken into account by computation by subtracting a specific sum from the measured values during processing of the recorded detector outputs from the respective scanning points.

SUMMARY OF OPERATION

As a specific example involving FIGS. 2 and 3, twenty-four detectors may be arranged in a ring as shown in FIG. 3 with fifteen degree intervals between the successive detectors, these successive detectors being directed to successive scatter volumes such as $V_1$, $V_2$, $V_3$, ... $V_{24}$, along the beam path 5 (in correspondence with the arrangement of scatter volumes in FIG. 1A). By way of example, the successive scatter volumes may have a center to center spacing of from one to two centimeters and corresponding to the resolution of the conical collimator such as indicated at K in FIG. 1. The anode voltage of the x-ray tube 2 is switched between voltage values $U_1$ and $U_2$ as described with reference to FIG. 1C and being between 150,000 volts and 500,000 volts. Beam energies are per se usable in the range up to a million electron volts and more such as can be produced in a betatron. In a specific example, potential $U_1$ is about 300,000 volts and is filtered by means of a filter such as indicated at $F_c$ in FIG. 1C formed of lead (Pb) of a thickness of one millimeter, while potential $U_2$ is at 200,000 volts and is applied via copper filter segments having a thickness of three millimeters. Each detector such as detector 7 in FIG. 2 thus receives alternately a high energy spectrum of scattered radiation $E_I$ and a low energy spectrum of scattered radiation $E_{II}$. As indicated for detector $D_c$ in FIG. 1C, a channel switching means for each detector supplies an electric pulse $J_I$ to a first recording chanel such as RCI, and supplies the alternate electric pulse $J_{II}$ resulting from the low energy spectrum of scattered radiation to a second separate recording channel such as $RC_{II}$. Thus, with twenty-four detectors, signal values such as $J_I$ and $J_{II}$ would be recorded for each of the twenty-four detectors on forty-eight separate recording channels. In order to obtain information regarding the ventilation of the lungs, the forty-eight channels may each record a time series of pulses, and the switching rate of the tube voltage, and the corresponding rate of operation of the filter $F_C$, FIG. 1C, and of the channel switching means such as CS, can be at a suitable high rate much greater than the breathing rate, so as to provide a detailed time sequence of density variations for each of the adjacent scatter volumes such as $V_1$ through $V_{24}$ as previously mentioned. The forty-eight channels of information are processed, taking into account the respective scattering angles theta ($\theta$). In this specific example the angles $theta_1$ through $theta_{24}$ formed by the detector axes such as 7a, FIG. 2, with the beam path 5 would all lie within a range between about thirty and forty-five degrees. Thus, with this specific example in accordance with FIGS. 2 and 3, time variations of density in twenty-four contiguous scatter volumes $V_1$ through $V_{24}$ can be recorded and subsequently processed to eliminate the effects of multiple scattering and of the successively different scattering angles theta, whereupon the processed information can be formed into a time sequence of pictures in an analogue or digital fashion, so as to visually represent the time variation of density along the beam path 5 during breathing of the patient in the suitable upright position as indicated in FIG. 2.

In an embodiment in accordance with FIGS. 4 and 5, a radiation source such as indicated at $S_a$ FIG. 1A, or $S_b$, FIG. 1B, may be utilized for radiation source 23 so as to produce a series of beams such as indicated at 37a from pill 37 in FIG. 4, along respective paths as indicated at $P_{b1}$, $P_{b2}$, $P_{b3}$, ..., $P_{b6}$ in FIG. 1B. The scattered radiation from volume $V_2$ in FIG. 1B, may be collected by detector 30 FIG. 4 which corresponds to detector 33-2, FIG. 1B. Similarly, the scatter radiation from the volume $V_2$ can be collected by the second detector of the upper level 31, FIG. 5, which is to the patient's left from the detector 28 as viewed in FIG. 4. The volume $V_3$ in FIG. 1B may have the conical collimators such as K, FIG. 1, of detector 28 and of detector 33-3 aligned therewith. With respect to the plane in FIG. 5 which coincides with the axes of detector 28 and detector 33-3, such plane will intersect path $P_{b3}$ at volume V3, and the detector axes will form equal angles in such plane with the axis of path $P_{b3}$. A similar relationship may prevail between the other correspondingly numbered detectors of rows 31 and 33, for example the first detector of row 31 and the corresponding detector 33-1 of row 33 having their axes intersecting path Pb1 at equal angles and at volume $V_1$, FIG. 1B. In a specific example with respect to FIGS. 4 and 5, the six scatter volumes $V_1$ through $V_6$, FIG. 1B, may occupy a width of the patient in a horizontal plane of thirty-five centimeters, so that if each scatter volume has an effective diameter of about two centimeters, then the separation between successive scatter volumes such as $V_1$ and $V_2$ may be a multiple of the scatter volume diameter, for example four centimeters, and the density of eighteen scatter volumes over a width of the patient of about forty centimeters could be obtained by shifting the patient 27 in a horizontal plane as represented by direction indication 25a in FIG. 4 in two successive steps of approximately 2 centimeters each. Successive scatter volumes $V_1'$ and $V_1''$ would thus be aligned with source 37-1 in the successive horizontal shifting movements of the patient in the direction of arrow 22a, FIG. 1B. With the arrangement of FIG. 1B, the detectors such as 33-1 through 33-3 in the upper and lower rows 31 and 33 of FIG. 5 may be moved jointly in the direction of arrow 23b while source $S_b$ and receivers 32-1 through 32-3 of row 32 remain stationary. On the other hand, for scanning in the direction of arrow 23a, FIG. 4, or with adjustment of the patient as indicated at 25a, the components 23 and 24 of FIG. 4 must move jointly or remain fixed, respectively, so as to preserve the precise alignment of the dectector axes with the primary beam paths $P_{b1}$, etc. Such independent horizontal adjustment of detectors $D_{b(n)}$ in FIG. 1B can be taken as being represented by dath line 23b' in FIG. 1B. The energytime diagrams of FIGS. 1A and 1B show transmission of ray energy (e.g. at $t_2$) after completion of an indexing step (e.g. indexing at $t_{12}$ between shutter-open intervals $t_1$ and $t_2$).

The embodiment of FIG. 6 may correspond to the embodiment of FIG. 1C except that the angles theta would be in excess of ninety degrees as illustrated for detectors 39 and 40.

In each of the embodiments as described, it is possible to obtain density measurements with sufficient accuracy for medical purposes at measurement depths along the primary beam path of substantially over eleven centimeters. In the embodiments such as FIGS. 4 and 6 where two or more detectors are aligned with a common point on the beam axis such as point 50, FIG. 6, it is advantageous to have the angles theta of the detector axes relative to the beam path equal, since in this case it is not necessary to convert the measurement results to equal angles, before averaging or otherwise accurately combining the results. For the sake of a diagramatic indication, detectors $D_c$ and $D_{c1}$ in FIG. 1C may be taken as corresponding to detectors 39 and 40 of FIG. 6. Means are diagramatically indicated at 51 for receiving the respective pulses $J_{I(1)}$ and $J_{II(1)}$ which are sequentially received from detectors $D_{c1}$ and separated by a means of parallel switching in the channel switching means CS. By way of example, the means 51 may comprise calibrating means for supplying signals to the component $Q_c$ identical to the signals $J_I$ and $J_{II}$ if a body of a uniform known density is substituted at $B_c$. Where the detector axes of detectors 39 and 40 form different angles with the beam 41, the means 51 may represent means for individually calibrating the signals $J_{I(1)}$ and $J_{II(1)}$.

Where the detector axes of FIGS. 4 and 5 form different means scattering angles $\theta$ with the primary beam paths, processing of the signals may adjust the respective outputs to correspond with the output of the detector having the lowest count rate (for example the detector having the highest value of scattering angle). For example, in FIG. 1A, if the angle $\theta$ of detector axis D$a$1 has the highest angle value, and if detector D$a$1 receives the lowest count rate, the outputs $Ns(n)$ of the other detectors may be adjusted by means indicated at 51$a$, such that for equal densities at volumes $V_1$ and $V_n$ and with other conditions uniform, the average adjusted pulse rate $N_{SI(n)}$ will substantially be equal to pulse rate $N_{SI}$ when measured over a time interval of suitable length. Similarly, adjusted pulse rates $N_{SII(n)}$ and $N_{SIII(n)}$ would correspond substantially to $N_{SII}$ and $N_{SIII}$, respectively, under such conditions. By way of example components 51$a$ may be binary fraction pulse rate multipliers having numbers of binary divider stages suitable to the desired accuracy. Thus with a homogeneous body of uniform density substituted at $B_a$ in FIG. 1A, the outputs $N_{SI(n)}$ for each further detector D$a(n)$ may be equalized with $N_{SI}$ for detector D$a$1, and the outputs $N_{SII(n)}$ and $N_{SIII(n)}$ will be similarly equalized. Thereafter during measurement for the body B$a$, the output pulse rates such as $N_{SI(n)}$, $N_{SII(n)}$ and $N_{SIII(n)}$ will be calibrated with those of detector D$a$1, and variations in pulse rate will be a function of density variations at $V_1$ through $V_n$ referenced to the scatter angle $\theta$ of detector D$a$1. All such equalized detector output signals $N_{SI(n)}$, $N_{SII(n)}$ and $N_{SIII(n)}$ are then recorded on respective individual channels for subsequent processing and graphical display. Of course signals $N_{S(n)}$ may be recorded without equalization and then be equalized to a common scatter angle during subsequent processing.

Similarly for FIG. 2, if detector 7 has a smaller scatter angle $\theta$ than detector 8, the pulses $J_{I(8)}$ and $J_{II(8)}$ (not shown) supplied by the channel switching means CS from detector 8 may be equalized by means indicated at 51, FIG. 1C, so that with a body of uniform density at $B_c$, the output pulses $J_{I(8)}$ and $J_{II(8)}$ would be equalized in amplitude with pulses $J_{I(7)}$ and $J_{II(7)}$, respectively, from detector 7 (not shown). The means 51 indicated in FIG. 1C may correspond to that indicated by reference numerals nine through twelve in the second figure of U.S. Pat. No. 3,904,874. A similar equalization could be effected in FIG. 6, where detectors 39 and 40 have different scatter angles. Equal scatter angles for detectors 39 and 40 are preferred since it is then unnecessary to equalize the signals to a common scatter angle value.

While presently preferred embodiments of the invention have been described with reference to FIGS. 2-6, it will be apparent that many modifications and variations may be effected without departing from the scope of the novel concepts of the present invention.

We claim as our invention:

1. The method of determining the density of bodies by means of penetrating rays, which comprises directing rays of plural preselected different wavelengths from at least one radiation source means to produce at least one beam of rays along a beam path extending from the source means to an internal region of the body whose density is to be measured, arranging detector means outside of said beam of rays for receiving scattered radiation from said internal region along respective detector axes which intersect said region and form respective angles other than an angle in the vincinity of zero degrees with said beam path, and responding to the scattered radiation received by said detector means along the respective detector axes to supply a plurality of output signals as a function thereof which output signals are responsive only to plural preselected wavelengths of scattered radiation as produced by the plural preselected different wavelengths from the source means.

2. The method of claim 1 wherein the method is further characterized by:

producing primary rays of different wavelengths from at least one radioactive source disposed in a shielded chamber, collimating the primary rays from said chamber so as to direct beams of such primary rays of different wavelengths along substantially a common straight line beam path extending directly to said internal region whose density is to be measured, sensing the scattered radiation from said region resulting from the respective beams of primary rays as received at said detector means, and producing respective separate output signals in response to the sensing of the respective scattered rays produced by the respective different wavelengths of primary rays.

3. The method of claim 2 with said primary rays being produced by means of a single isotope in said chamber which supplies rays of respective different quantum energies.

4. The method of claim 3 with said chamber containing iridium 192 (Ir$^{192}$) for producing primary rays at quantum energies of 310,000 electron volts (310 keV) and 468,000 electron volts (468 keV).

5. The method of claim 2 with said primary rays being produced by means of a plurality of radioactive isotopes in a common shielded chamber.

6. The method of claim 5 with said common shielded chamber containing iridium 192 (Ir$^{192}$) and cesium 137 (Cs$^{137}$) with respective activities for producing approximately equal numbers of scattered rays at three respective different average quantum energies at said detector means.

7. The method of claim 2 with said primary rays being produced by radioactive source means having an activity of about $111 \times 10^{10}$ per second (thirty Ci).

8. The method of claim 2 with said primary rays being produced by means of a plurality of radioactive isotopes having activities in the range from about $37 \times 10^{10}$ per second (ten Ci) to about $111 \times 10^{10}$ per second (thirty Ci).

9. The method of claim 2 wherein the method is further characterized by the step of forming a resultant signal as a function of the quotient of said separate output signals.

10. The method of claim 1 wherein the method is further characterized by producing primary rays of different wavelengths by means of an X-ray source which is sequentially operated at respective different energy levels to produce respective time sequential output signals at said detector means.

11. The method of claim 10 with said X-ray source being operated sequentially at respective voltages of about 300,000 volts (300 kV) and 200,000 volts (200 kV).

12. The method of claim 10 with said X-ray source being operated at a relatively higher electric potential and supplying its radiation via a lead (Pb) filter with a thickness of about one millimeter (1 mm) and at a relatively lower electric potential to supply radiation via a filter of copper (Cu) having a thickness of about three millimeters (3 mm).

13. The method of claim 1 with said method being further characterized by relatively shifting the detector means and the body such that the detector means scans successive internal regions in a layer of said body and produces respective time sequences of said output signals.

14. The method of claim 13 wherein the relative shifting step produces a relative scanning speed in said layer from about five centimeters per second to about ten centimeters per second.

15. The method of claim 1 wherein the method is further characterized by producing primary rays of a plurality of different energy spectrums from at least one source, collimating the primary rays from said source so as to direct beams of such primary rays of different energy spectrums along substantially a common beam path extending directly to said internal region whose density is to be measured, arranging detector means for receiving scattered radiation along respective detector axes which intersect said region at substantially a common point, sensing the scattered radiation from said common point in said region resulting from the respective beams of primary rays as received at the respective detector means, and producing respective separate output signals from each of the detector means in response to the sensing of the respective scattered rays produced by the respective different energy spectrums of primary rays.

16. The method of claim 1 wherein the method is further characterized by producing primary rays of different wavelengths by means of an x-ray source which is sequentially operated at respective different energy levels, and arranging detector means for receiving scattered radiation along respective detector axes which intersect said beam path at substantially a common point to produce respective time sequential output signals at each of said detector means.

17. The method of claim 16 with said x-ray source being operated sequentially at respective voltages of about 300,000 volts (300 kV) and 200,000 volts (200 kV).

18. The method of claim 16 with said x-ray source being operated at a relatively higher electric potential and supplying its radiation via a lead (Pb) filter with a thickness of about one millimeter (1 mm) and at a relatively lower electric potential to supply radiation via a filter of copper (Cu) having a thickness of about three millimeters (3 mm).

19. The method of claim 1 with said method being further characterized by arranging the detector means to receive scattered radiation along respective detector axes which intersect said beam path at substantially a common point, and relatively shifting the detector means and the body such that each detector means scans successive points of said internal region of said body and produces a time sequence of said output signals.

20. The method of claim 19 wherein the relative shifting step produces a relative scanning speed in said region from about five centimeters per second to about ten centimeters per second.

21. The method of claim 1 further characterized by arranging respective detector means for receiving scattered radiation from said internal region along respective detector axes which intersect said region at successive points therein, and responding to the scattered radiation received by the respective detector means along the respective detector axes to supply a plurality of separate output signals for individual processing in the determination of the respective densities in the vicinity of the respective points.

22. The method of claim 21, wherein the method is further characterized by producing primary rays of different wavelengths from a plurality of radioactive sources, directing beams from the respective sources along respective substantially common beam paths extending directly to said internal region, and arranging respective detector means for receiving scattered radiation from said internal region along respective detective axes which intersect said region at respective points on the respective substantially common beam paths.

23. The method of claim 22 with said primary rays from each of the sources being produced by means of a single isotope which supplies rays of respective different quantum energies.

24. The method of claim 23 with said chamber containing iridium 192 ($Ir^{192}$) for producing primary rays at quantum energies of 310,000 electron volts (310 keV) and 468,000 electron volts (468 keV).

25. The method of claim 22 with said primary rays being produced by radioactive source means having an activity of about $111 \times 10^{10}$ per second (thirty Ci).

26. The method of claim 22 wherein the method is further characterized by the step of forming a resultant signal as a function of the quotient of said separate output signals.

27. The method of claim 21 wherein the method is further characterized by sensing the scattered radiation from successive points along said beam path in said region as received by respective detector means, and producing respective separate output signals from each of said detector means in response to the sensing by such detector means of the respective scattered rays.

28. The method of claim 27 wherein the method is further characterized by producing primary rays of different wave lengths by means of a plurality of radioactive isotopes in a common shielded chamber, directing said primary rays along substantially a common beam path, and sensing the scattered radiation from successive points along said common beam path in said region.

29. The method of claim 28 with said common shielded chamber containing iridium 192 ($Ir^{192}$) and cesium 137 ($Cs^{137}$) with respective activities for producing approximately equal numbers of scattered rays at three respective different average quantum energies at said detector means.

30. The method of claim 21 wherein the method is further characterized by producing primary rays of different wave lengths by means of an x-ray source which is sequentially operated at respective different energy levels to produce time sequential output signals, and arranging respective detector means for receiving scattered radiation corresponding to operation of said source at the respective different energy levels to produce respective time sequential output signals at each of said detector means for individual processing.

31. The method of claim 30 with said x-ray source being operated sequentially at respective voltages of about 300,000 volts (300 kV) and 200,000 volts (200 kV).

32. The method of claim 21 wherein the method is further characterized by producing the primary rays of different wave lengths by means of an x-ray source which is sequentially operated at respective different energy levels to produce alternating beams of rays along a beam path of the respective different energy levels, arranging respective detector means for receiving scattered radiation along respective detector axes which intersect said beam path at successive points therealong, and responding to the scattered radiation received by the respective detector means to produce respective time sequential output signals at each of said detector means for individual processing in the determination of the density in the vicinity of the associated point on said beam path.

33. The method of claim 21 with said method being further characterized by relatively shifting the detector means and the body such that the detector means scan successive series of points in a layer of said body and produce respective time sequences of said output signals for individual processing in the determination of the respective densities in the vicinity of the respective series of points.

34. The method of claim 33 wherein the relative shifting step produces a relative scanning speed in said layer from about 5 centimeters per second to about 10 centimeters per second.

35. The method of claim 1 further characterized by arranging respective detector means outside of said beam of rays with the detector axes intersecting said region at a common point, and each forming an angle other than an angle in the vicinity of zero degrees with said beam path, and responding to the radiation received by the respective detector means to supply a plurality of separate output signals for individual processing in the determination of the density at such common point.

36. The method of claim 1 further characterized by arranging respective detector means outside of said beam of rays with the detector axes intersecting said region at a common point, and forming respective equal angles other than an angle in the vicinity of zero degrees with said beam path.

37. The method of claim 1 further characterized by directing rays of different wavelengths from each of a series of radiation sources along respective beam paths intersecting said region, and arranging respective detector means outside of the beam of rays along each of said beam paths for receiving scattered radiation along respective detector axes which intersect the respective beam paths.

38. The method of claim 37 further characterized by arranging respective pluralities of point-focused detectors with their detector axes intersecting respective common points on the respective beam paths.

39. Radiobiological examination apparatus for determining the density of bodies by means of penetrating rays, which comprises radiation source means for directing beams of rays of plural preselected different wavelengths into a region of the body whose density is to be measured, with the beams of rays of said plural preselected different wavelengths each being transmitted along a beam path to the region, detector means disposed outside of said beams of rays and having respective detector axes intersecting said region and forming respective angles other than an angle of zero degrees with said beam path for receiving scattered radiation from said region, and respective signal supply means responsive to the scattered radiation received by said detector means along the respective detector axes to supply a plurality of output signals as a function of radiation scattered from such region which output signals are responsive only to plural preselected wavelengths of said scattered radiation as produced by the beams of said plural preselected different wavelengths from said source means.

40. Radiobiological examination apparatus according to claim 39 with scanner means including support means for supporting the body to be examined and mounting means for mounting said radiation source means and said detector means and providing for the shifting of the support means relative to said mounting means such that successive regions of the body lying generally in a layer are successively scanned to provide time sequences of said output signals.

41. Radiobiological examination apparatus in accordance with claim 40 with motorized drive mechanism forming part of said scanner means for producing shifting of the support means relative to said mounting means.

42. Radiobiological examination apparatus in accordance with claim 39 with a patient support means for supporting the body of a patient in operative relation, said patient support means comprising a seat arranged to be straddled by the patient.

43. Radiobiological examination apparatus according to claim 42 further comprising motorized drive mechanism for producing relative shifting movement between said patient support means and said source and detector means such that successive regions of the patient's body lying generally in a layer are successively scanned to provide time sequences of said output signals.

44. Radiobiological examination apparatus in according with claim 39 with a motorized drive mechanism for producing relative shifting movement between a body to be examined and said source and detector means such that successive regions of the body are scanned at a scanning speed in the range from about five centimeters per second to about ten centimeters per second.

45. Apparatus according to claim 39 with radiation source means for directing beams of rays of different wavelengths along a common beam path, detector means disposed outside of said beams of rays and having respective detector axes intersecting said common beam path at respective points therealong, and respective signal supply means responsive to the scattered radiation received by the respective detector means from the respective points to supply output signals as a function of radiation scattered from the respective points.

46. Apparatus according to claim 45 with scanner means including support means for supporting the body to be examined and mounting means for mounting said detector means and providing for the shifting of the support means relative to said mounting means such that successive series of points lying generally in a layer are successively scanned to provide time sequences of said output signals.

47. Apparatus in accordance with claim 46 with motorized drive mechanism forming part of said scanner means for producing shifting of the support means relative to said mounting means.

48. Apparatus in accordance with claim 45 with a patient support means for supporting the body of a patient in operative relation, said patient support means comprising a seat arranged to be straddled by the patient.

49. Apparatus according to claim 48 further comprising motorized drive mechanism for producing relative shifting movement between said patient support means and said detector means such that successive series of points lying generally in a layer are successively scanned to provide time sequences of said output signals.

50. Apparatus in accordance with claim 45 with a motorized drive mechanism for producing relative shifting movement between a body to be examined and said detector means such that successive series of points are scanned at a scanning speed in the range from about five centimeters per second to about ten centimeters per second.

51. Apparatus according to claim 45 with said source means comprising a series of sources for directing beams of rays along respective common beam paths, and said detector means comprising a series of point-focus detectors having detector axes substantially intersecting the respective beam paths at respective scatter volumes, for receiving scattered radiation from the respective scatter volumes.

52. Apparatus according to claim 51 with two point-focus detectors having detector axes intersecting each scatter volume.

53. Apparatus according to claim 52 with said two detectors having their detector axes forming equal angles with the common beam path substantially intersected thereby.

54. Apparatus according to claim 15 with said detector means comprising point-focus detectors with detector axes forming unequal angles with said beam path, and respective signal supply means connected with the respective detectors for supplying respective output signals therefrom for individual processing.

55. Apparatus according to claim 15 with said detector means being disposed outside of said beams of rays and having respective detector axes intersecting said region at a common point and forming respective angles other than an angle of zero degrees with said beam path for receiving scattered radiations from said common point, respective signal supply means responsive to the scattered radiation received by said detector means along the respective detector axes from said common point to supply a plurality of output signals as a function of radiation scattered from such region, and processing means coupled to said supply means for separately processing each of said output signals.

56. Apparatus according to claim 55 with scanner means including support means for supporting the body to be examined and mounting means for mounting said detector means and providing for the shifting of the support means relative to said mounting means such that successive points of the body lying along said beam path are successively scanned to provide time sequences of said output signals.

57. Apparatus in accordance with claim 56 with motorized drive mechanism forming part of said scanner means for producing shifting of the support means relative to said mounting means.

58. Apparatus in accordance with claim 55 with a patient support means for supporting the body of a patient in operative relation, said patient support means comprising a seat arranged to be straddled by the patient.

59. Apparatus according to claim 58 further comprising motorized drive mechanism for producing relative shifting movement between said patient support means and said detector means such that successive regions of the patient's body lying along said beam path are successively scanned to provide time sequences of said output signals.

60. Apparatus in accordance with claim 55 with a motorized drive mechanism for producing relative shifting movement between a body to be examined and said detector means such that successive regions of the body are scanned at a scanning speed in the range from about five centimeters per second to about ten centimeters per second.

* * * * *